(12) United States Patent
Kalinowski et al.

(10) Patent No.: US 6,754,632 B1
(45) Date of Patent: Jun. 22, 2004

(54) METHODS AND DEVICES FOR DELIVERING EXOGENOUSLY GENERATED SPEECH SIGNALS TO ENHANCE FLUENCY IN PERSONS WHO STUTTER

(75) Inventors: Joseph Kalinowski, Greenville, NC (US); Andrew Stuart, Winterville, NC (US); Michael Rastatter, Greenville, NC (US)

(73) Assignee: East Carolina University, Greenville, NC (US)

(*) Notice: Subject to any disclaimer, the term of this patent is extended or adjusted under 35 U.S.C. 154(b) by 681 days.

(21) Appl. No.: 09/665,192

(22) Filed: Sep. 18, 2000

(51) Int. Cl.[7] .................................................. A61F 5/58
(52) U.S. Cl. ........................................ 704/271; 600/23
(58) Field of Search ............................... 704/270, 271; 600/23, 24; 434/185

(56) References Cited

U.S. PATENT DOCUMENTS

| | | |
|---|---|---|
| 3,349,179 A | 10/1967 | Klein |
| 3,566,858 A | 3/1971 | Larson et al. |
| 3,773,032 A | 11/1973 | Donovan et al. |
| 3,920,903 A | 11/1975 | Beller |
| 4,336,524 A | 6/1982 | Levine |
| 4,421,488 A | 12/1983 | Parlenvi et al. |
| 4,464,119 A | 8/1984 | Vildgrube et al. |
| 4,636,866 A | 1/1987 | Hattori |
| 4,685,448 A * | 8/1987 | Shames et al. ............... 600/23 |
| 4,695,129 A | 9/1987 | Faessen et al. |
| 4,784,115 A | 11/1988 | Webster |
| 4,856,045 A | 8/1989 | Hoshina |
| 4,916,441 A | 4/1990 | Gombrich |
| 4,934,773 A | 6/1990 | Becker |
| 5,003,300 A | 3/1991 | Wells |
| 5,048,077 A | 9/1991 | Wells et al. |
| 5,106,179 A | 4/1992 | Kamaya et al. |
| 5,111,498 A | 5/1992 | Guichard et al. |
| 5,138,312 A | 8/1992 | Tsukakmoto et al. |
| 5,189,632 A | 2/1993 | Paajanen et al. |
| 5,281,957 A | 1/1994 | Schoolman |
| 5,347,400 A | 9/1994 | Hunter |
| 5,478,304 A | 12/1995 | Webster |
| 5,485,318 A | 1/1996 | Lebby et al. |
| 5,485,504 A | 1/1996 | Ohnsorge |
| 5,561,538 A | 10/1996 | Kato et al. |
| 5,596,451 A | 1/1997 | Handschy et al. |
| 5,794,203 A | 8/1998 | Kehoe ........................ 704/271 |
| 5,828,427 A | 10/1998 | Faris |
| 5,940,798 A | 8/1999 | Houde ........................ 704/271 |
| 5,961,443 A | 10/1999 | Rastatter et al. |
| 6,073,034 A | 6/2000 | Jacobsen et al. |
| 6,231,500 B1 * | 5/2001 | Kehoe ........................ 600/23 |

OTHER PUBLICATIONS

Perkins, "From Pscyhoanalysis to Discoordination," H.H. Gregory (Ed.) "Controverises About Stuttering Therapy," pp. 97–127, University Press (1979).

(List continued on next page.)

*Primary Examiner*—Richemond Dorvil
*Assistant Examiner*—Martin Lerner
(74) *Attorney, Agent, or Firm*—Myers Bigel Sibley & Sajovec PA

(57) ABSTRACT

Methods and devices generate an exogenous natural second speech signal as an auditory stimulus to a user to enhance the fluency of persons who stutter. The natural speech signal is independent of the contemporaneous speech production of the stutterer and is provided by a voice gesture and can be a prolonged or sustained voice gesture sound such as a simple vowel, or consonant, or vowel trains and the like. The second speech signal can be transmitted in advance of a speaking event or speech production of the stutterer and/or concurrently with a speaking event, either intermittently or continuous during the speaking event. The devices of the instant invention are configured to provide the voice based speech signal such that it is audible to the user and does not require feedback of the user's own speech allowing the user to speak at a substantially normal pace with enhanced fluency. The device and methods can relay the signal based on a manual activation or automatically based on a detection of speech or a stuttering event on the part of the user.

65 Claims, 8 Drawing Sheets

OTHER PUBLICATIONS

Perkins, "Phone Rate and the Effective Planning Time Hypothesis of Stuttering," 29. Jnl. Of Speech and Hearing Res., 22, pp. 747–755 (Dec. 1979).

Puce et al., "Differential Sensitivity of Human Visual Cortex to Faces, Letterstrings, and Textures: A Functional Magnetic Resonance Imagine Study," J. Neuroscie, vol. 16, No. 16, pp. 5205–5215 (Aug. 15, 1996).

Sams et al., "Face–Specific Response from the Human Inferior Occipito–Temporal Cortex," Neurosci., vol. 77, No. 1, pp. 49–55 (1997).

Sams et al., "Seeing speech; visual information from lip movements modifies activity in the human auditory cortex," Neuroscience Letters, vol. 127, pp. 141–145 (1991).

Stuart et al., "Fluent Speech, Fast Articulatory Rate, and Delayed Auditory Feedback: Creating a Crisis for a Scientific Revolution?" Perceptual and Motor Skills, 82, pp. 211–218 (1996).

Tye–Murray, "Visual feedback during speech production," J. Acoust. Soc. Am., vol., 79, No. 4, pp. 1169–1171 (Apr. 1986).

Wu et al., "A Position Emission Tomograph [18FDeoxyglucose Study of Developmental Stuttering," Neuroreport, 6, pp. 501–505 (1995).

Hargrave et al., "Effect of Frequency–Altered Feedback on Stuttering Frequency at Normal and Fast Speech Rates," J. of Speech and Hearing Res., 37, pp. 1113–1119 (Dec. 1994).

Howell et al., "Automatic Recognition of Repetitions and Prolongations in Stuttered Speech," C. W. Starkweather and H.F.M. Peters (Eds.), Proceedings of the First World Congress on Fluency Disorders, vol. II, pp. 372–374), The Netherlands University Press, Nijmegen (1995).

Howell et al., "Automatic Stuttering Frequency Counts," W. Hulstijn, et al. (Eds.), Speech Production: Motor Control, Brain Research and Fluency Disorders, Amsterdam, Elsevier Science, pp. 395–404 (1997).

Howell et al., "Development of a Two–Stage Procedure for the Automatic Recognition of Dysfluencies in the Speech of Children Who Stutter: II. ANN Recognition of Repetitions an Prolongations with Supplied Word Segment Markers," Journal of Speech, Language and Hearing Research, 40(5), pp. 1085–1096 (Oct. 1997).

Howell et al., "Development of a Two–Stage Procedure for the Automatic Recognition of Dysfluencies in the Speech of Children Who Stutter: I. Psychometric Procedures Appropriate for Selection of Training Material for Lexical Dysfluency Classifiers," Journal of Speech, Language and Hearing Research, 40(5), pp. 1073–1084 (Oct. 1997).

Jayant, Nikil et al., "Signal Compression Based on Models of Human Perception," Proceedings of the IEEE, vol. 81, No. 10, pp. 13851422 (1993).

Johnson et al., "Studies in the Psychology of Stuttering: VII. Effect of Certain Changes in Speech Pattern Upon Frequency of Stuttering," J. Speech Disord., 2, pp. 105–109 (1937).

Kalinowski et al., "Effect of Normal and Fast Articulatory Rates on Stuttering Frequencey," J. Of Fluency Disorders, 20, pp. 293–302 (1995).

Kalinowski et al., "Stuttering Amelioration at Various Auditory Feedback Delays and Speech Rates," European Journal of Disorders of Communications, 31, pp. 259–269 (1996).

Kalinowski et al., "Effects of Alterations in Auditory Feedback and Speech Rate on Stuttering Frequency," Language and Speech, 36 (1), pp. 1–16, (1993).

Kalinowski et al., "Inducement of Fluent Speech in Persons Who Stutter Via Visual Choral Speech," Neurosci. Lett., 280, pp. 1–3 (2000).

Kuniszyk–Jozkowiak et al., "Effect of Acoustical, Visual, and Tactile Echo on Speech Fluency of Stutters," Folia Phoniatr. Lopgop., 48, pp. 193–200 (1996).

Massaro et al., "Evaluation and Integration of Visual and Auditory Information in Speech Perception," Journal of Experimental Psychology, Human Perception and Performance, vol. 9, No. 5, pp. 753–771 (1983).

Massaro et al., "Perception of asynchronous and conflicting visual and auditory speech," J. Acoust. Soc. Am. vol. 100, No. 3, pp. 1777–1786 (Sep. 1996).

McGurk et al., "Hearing lips and seeing voices," Reprinted from Nature, vol. 264, pp. 746–748 (1976).

MacLeod et al., "Effects of Single and Combined Altered Auditory Feedback on Stuttering Frequency At Two Speech Rates," J. of Commun. Disorders, 28, pp. 217–228 (1995).

May et al., "Some Effects of Masking and Eliminating Low Frequency Feedback on the Speeck of Stammerers," Behav. Res. & Therapy, 6, pp. 219–223 (1968).

"New Wired Clothing Comes with Personal Network," cnn.com/2000/TECH/computing/8/18/wired.jacket.idg/index.html (posted on Aug. 18, 2000).

"Excuse me, is that a monitor on your head?", CNN.com, http://www.cnn.com/2000/TECH/computing/03/31/head.monitor.idg/index.hml (Aug. 30, 2000).

"Visions of wearable Internet ware," CNN.com, http://www.cnn.com/2000/STYLE/fashion 06/26/wearable.computers/index.html (Aug. 30, 2000).

Adams et al., "The Effects of Auditory Masking on the Anxiety Level, Frequency of Dysfluency, and Selected Vocal Characteristics of Stutterers," J. Speech Ear. Res., 15, pp. 572–578 (1972).

Adams, Martin, "Comment on 'Interpreting Results of the Fluent Speech Paradigm in Stuttering Research: Difficulties in Separating Cause From Effect,'" Letters to the Editor, J. Speech Hear. Res., 37, pp. 813–815 (1994).

Andrews et al. "Stuttering: A Review of Research Findings and Theories," circa 1982, J. Speech Hear. Disord., 48, pp. 226–246 (Aug. 1983).

Andrews et al., "Stuttering: Speech Pattern Characteristics Under Fluency–Inducing Conditions," J. Speech Hear. Res., 25, pp. 208–215 (Jun. 1982).

Armson et al., "A Model of Stuttering Remediation: Multiple Factors Underlying Fluency Enhancement," In C.W. Starkweather and H.F.M. Peters (Eds.), Stuttering: Proceedings from The First World Congress on Fluency Disorders, University Press, Nijmegen, The Neterlands, pp. 296–300 (1995).

Bakker, K. "Clinical Technologies for the Reduction of Stuttering and Enhancement of Speech Fluency," Seminars in Speech and Language, 20 (3), pp. 271–279 (1999).

Barber, V. "Studies in the Psychology of Stuttering: XV. Chorus Reading as a Distraction in Stuttering," J. Speech Disord., 4, pp. 371–383 (1939).

Calvert et al., "Activation of Auditory Cortex During Silent Lipreading," Science, vol. 276, pp. 593–596 (Apr. 25, 1997) http://www.scienemag.org.

Cherry et al., "Experiments Upon Total Inhibition of Stammering by External Control and Some Clinical Results," J. Psychosom. Res., 1, pp. 233–246, (1956).

Conture, E.G., "Some Effects of Noise on the Speaking Behavior of Stutterers," J. Speech Hear. Res., 17, pp. 714–723 (1974).

Dodd, "Interaction of auditory and visual information in speech perception," British Journal of Psychology, vol. 71, pp. 541–549 (1980).

Erber, "Auditory–Visual Perception of Speech," Journal of Speech and Hearing Disorders, pp. 481–492 (1975).

Fox et al., "A Pet Study of the Neural Systems of Stuttering," Nature, 382, pp. 158–161 (Jul. 11, 1996).

International Search Report, Int'l Appl. No. PCT/US00/34547, mailed Apr. 4, 2001.

Dayalu et al. (2001). *Producing the Vowel/a/Prior to Speaking Inhibits Stuttering in Adults in the English Lanugage.* Neuroscience Letters; vol. 306, Issues 1–2, pp. 111–115.

Glover et al. (1996). *Effect Of Instruction To Sing On Stuttering Frequency At Normal And Fast Rates.* Perceptual and Motor Skills, 83, pp. 511–522.

Kalinowski et al. (2002). *Inducement of fluent speech in persons who stutter via visual choral speech.* Neuroscience Letters, vol. 281, Issues 2–3, pp. 198–200.

Kalinowski et al. (2001). *Re: Second Speech Signals Versus Prolonged Speech Techniques: A Reply to Onslow.* Int. J. Lang. Comm. Dis., 3 pages.

Kalinowski et al. (2000). *Stutter–free and stutter–filled speech signals and their role in stuttering amelioration for English speaking adults.* Neuroscience Letters 293: pp. 115–118.

Kalinowski et al. (2003). *Choral Speech: The Amelioration of Stuttering via Imitation and the Mirror Neuronal System.* Neuroscience and Behavioral Reviews 27, pp. 339–347.

Kalinowski, J., & Saltuklaroglu, T. (2003). *Speaking with a mirror: engagement of mirror neurons via choral speech and its derivatives induces stuttering inhibition,* Medical Hypotheses, 60, pp. 538–543.

Saltuklaroglu et. al. (2003). *Say It With Me: Stuttering Inhibited,* Journal of Clinical and Experimental Neuropsychology, pp. 1–8.

Saltuklaroglu et al. (2002). *Reduction of stuttering: the dual inhibition hypothesis.* Medical Hypotheses, 58(1), pp. 67–71.

Saltuklaroglu et al. (In Press). *A Temporal Window for the Central Inhibition of Stuttering Via Exogenous Speech Signals in Adults.* Neuroscience Letters 20238, Jul. 31, 2003, pp. 1–5.

Stuart et al. (1996). *Fluent Speech, Fast Articulatory Rate, And Delayed Auditory Feedback: Creating A Crisis For A Scientific Revolution?.* Perceptual and Motor Skills, 82, pp. 211–218.

* cited by examiner

METHODS AND DEVICES FOR DELIVERING EXOGENOUSLY GENERATED SPEECH SIGNALS TO ENHANCE FLUENCY IN PERSONS WHO STUTTER

FIELD OF THE INVENTION

The present invention relates to devices and methods for enhancing the fluency of persons who stutter.

BACKGROUND OF THE INVENTION

Conventionally, stuttering has been treated by several different types of treatment, including psychiatric therapy, drug therapy, and the use of altered auditory feedback, generated by electrical signal processing devices, relayed to the person who stutters. These techniques can be generally characterized as either endogenous alterations of the speech signal output, such as prolonged or slowed speech, rhythmic speech, signing, and lipped speech, or exogenous dynamic alterations of the speech signal itself, both of which can successfully induce relatively fluent speech in people who stutter. See, e.g., O. Bloodstein, A *Handbook on Stuttering* ($5^{th}$ ed. Singular, San Diego, Calif., 1995).

It is believed that exogenous auditory alterations of speech, such as chorus reading, shadow speech, delayed auditory feedback, and frequency altered feedback, or a visual modality of treatment, such as visual choral speech, can generally produce more powerful and natural sounding reductions in stuttering than incongruous non-speech auditory inputs, such as masking noise and clicking, or visual inputs, such as flashing lights.

Two types of altered auditory feedback which have been used to treat stuttering include delayed auditory feedback ("DAF") and the introduction of a masking noise or masked auditory feedback ("MAF"). Generally described, DAF imposes a delay on the delivery of a feedback speech signal to a speaker/stutterer, while MAF serves to compete with a speaker's auditory feedback.

For example, M. E. Wingate, in *Stuttering: theory and treatment*, p. 237 (Irvington, 1976), describes a type of altered auditory feedback which can include DAF to provide emphasis on phonation, i.e., slowing speech down to extend syllable duration. However, this type of auditory feedback or fluency enhancement is conventionally thought to be achievable with or without the use of DAF as long as syllable prolongation was employed. See, e.g., W. H. Perkins, *From Psychoanalysis to Discoordination*, in H. H. Gregory (Ed.) *Controversies about stuttering therapy*, pp. 97–127 (University Press, 1979). See also Andrew Stuart et al., *Fluent Speech, Fast Articulatory Rate, and Delayed Auditory Feedback: Creating a Crisis for A Scientific Revolution?*, 82 Perceptual and Motor Skills, pp. 211–218 (1996).

Generally stated, the reduction in stuttering frequency under speech signal alterations has been attributed to entrained rhythm, distraction, modified vocalization, and rate reduction. Indeed, in the past, slowed speech rates were found to be an important factor in the reduction of stuttering. For example, in W. H. Perkins et al., *Phone rate and the effective planning time hypothesis of stuttering*, 29 Jnl. Of Speech and Hearing Research, 747–755 (1979), the authors reported that stuttering was virtually eliminated when speakers reduced speech by approximately 75%. However, other reports have found that rate reduction is neither necessary, nor sufficient, for fluency enhancement. See Kalinowski, et al., *Stuttering amelioration at various auditory feedback delays and speech rates*, European Journal of Disorders of Communication, 31, 259–269 (1996); Stuart et al., *Fluent speech, fast articulatory rate, and delayed auditory feedback: Creating a crisis for a scientific revolution?*, Perceptual and Motor Skills, 82, 211–218 (1996); MacLeod, et al., *Effect of single and combined altered auditory feedback on stuttering frequency at two speech rates*, Journal of Communication Disorders, 28, 217–228 (1995); Kalinowski et al., *Effect of normal and fast articulatory rates on stuttering frequency*, Journal of Fluency Disorders, 20, 293–302 (1995);. Hargrave et al, *Effect of frequency altered feedback on stutterers' fluency at two speech rates*, Journal of Speech and Hearing Research, 37, 1113–1119 (1994); and Kalinowski et al., *The effects of alterations in auditory feedback on stuttering frequency*, Language and Speech, 36, 1–16 (1993).

Recently, a portable therapeutic device and related stuttering enhancement treatment methods were described in U.S. Pat. No. 5,961,443 to Rastatter et al., the contents of which are hereby incorporated by reference as if recited in full herein. These devices and methods employ altered auditory feedback (auditory delay and/or frequency shift signals) to be delivered to a stutterer via a portably configured device. Despite the above, there remains a need to provide improved methods and devices for treating stuttering to enhance fluency in an effective easily implemented manner.

SUMMARY OF THE INVENTION

These and other objects are satisfied by the present invention by methods and devices which employ a "second" exogenously generated speech signal which is produced by a sound or sounds corresponding to spoken vocal utterances or natural speech (independent of the in situ uttered speech of the speaker/stutterer). The second exogenous speech signal can alternatively be generated by other than spoken speech so as to simulate natural speech sounds (such as generated electronically, mechanically, or electromechanically); these simulated sound(s) should be configured to simulate the voice gestures which trigger the auditory cortex of the speaker. The second speech signal of the instant invention can be used as an alternative to DAF or MAF, which typically manipulates, alters, or interferes or competes with the contemporaneous speech of the speaker himself (or herself). The second speech signal of the instant invention is an auditory stimulus which is a spoken speech signal (that is, a voice gesture associated with a vocal cord of a person). The second speech signal can be either stuttered or fluent, and/or coherent (a string of meaningful sounds forming words) or incoherent (the sound(s) having no understandable or meaningful content).

Preferably, the second speech signal comprises a prolonged uttered or spoken sound associated with a natural voice gesture such as a single syllabic vowel or consonant or a combination of vowels and/or consonants. The second speech signal of the instant invention can be relayed to the user such that it is intermittent, sustained for a determined period of time, or substantially continuous with the speech production of a user/patient undergoing treatment for stuttering.

Preferably, the second or exogenously generated auditory speech signal of the instant invention is generated exogenously by someone other than the speaker or patient/ stutterer (or generated by a device which can substantially replicate a vocal tract output in order to trigger the auditory cortex of the speaker, as noted above). It is also preferred that the second speech signal be recorded and stored in advance of use such that it can be conveniently and reliably provided or audibly relayed to the speaker at a desirable time (and repeatable at appropriate times).

In one embodiment, the exogenously generated second speech signal is a spoken prolonged speech sound (such as the last sound in the word "sudden"). It is more preferred that the prolonged speech sound is a steady state single syllabic sound. It is still more preferred that the prolonged speech sound is a vocal tract output associated with producing a steady state vowel sound. The exogenously generated speech signal can be provided at the start of speech of a person or patient prone to stuttering and/or episodically during speech, such as when a person starts to stutter or is experiencing a stuttering event, or even just at intervals during fluent speech to inhibit the onset of a stuttering event.

The second speech signal can be provided as an arrangement of different voice gesture sounds, the output of which can be varied to alter the exogenously generated speech signal auditory stimulus provided to the patient, over time.

In preferred embodiments, the second or exogenously generated speech signal is pre-recorded and relayed to the user at a desired or appropriate times (either as activated by user input or automatically activated upon detection of a stuttering event). The volume and/or duty cycle of the output are preferably variable to allow a user to adjust the output to his or her needs. That is, in one embodiment, the user can increase or decrease the duration or frequency of the transmitted second speech signal from a continuum ranging from continuously outputting the signal during speech production or a desired output time period to intermittently outputting the signal at desired adjustable intervals during the desired output period.

The second speech signal can be held in and delivered by portable miniaturized devices such as ITE (in the ear), BTE (behind the ear) or OTE (over the ear) stuttering aid devices. Alternatively, the second speech signal auditory stimulus can be generated from stand-alone handheld devices with speakers (or provided as an audio medium such as a compact disk or tape, or downloadable computer code, or other computer readable program formats) or incorporated into communication devices having voice or microphone inputs (such as the handset or base of a telephone or wireless telephone body, two way headsets, and the like) or other devices such as writing implements and the like. In other embodiments, the second speech signal can be held in or incorporated into an audio chip or DSP incorporated into (wrist) watches, bracelets, lapel pins, necklaces or other proximately worn (within the audible range of the user) jewelry such as necklaces and earrings, or headbands, hats, and the like.

One aspect of the invention is a method for enhancing the fluency of persons who stutter, comprising the steps of (a) exogenously generating a speech signal (independent of the contemporaneous speech production of a patient); (b) producing speech by the patient having a propensity to stutter; and (c) delivering the exogenously generated speech signal to the patient temporally proximate to the producing step such that the exogenous speech signal is audible thereto.

In a preferred embodiment, the exogenously generated speech signal is stored or pre-recorded to be repeatedly played back and/or audibly transmitted to the patient at desired intervals or at appropriate times. It is also preferred that the exogenous or second speech signal be generated by a person other than the patient.

Another aspect of the present invention is directed to a device to enhance the fluency of persons who stutter. The device comprises an audio storage medium comprising at least one pre-recorded auditory stimulus speech signal thereon and a speaker operably associated with the audio storage medium to output the speech signal therefrom. The device also includes a power source in communication with the audio storage medium and speaker and an activation switch operably associated with the power source. The device is configured such that the auditory stimulus or second speech signal can be repeatedly output to a user at desired times corresponding to at least one of during an episodic stuttering event; in advance of a speaking event (the production of speech on the part of the user); and during a speaking event to thereby provide an auditory stimulus to the user/person who stutters to enhance the fluency of speech thereof.

In a preferred embodiment, the device includes a user input trigger switch operably associated with the speaker. The user input trigger switch is configured to accept user input to initiate a substantially immediate delivery of the auditory stimulus (second speech signal) such that it is audible to the user. The device can also include an intermittent output switch or button that can allow a user to determine the length, or repeating cycle of the transmitted output signal (to allow the user to vary the auditory stimulus). Similarly, the device can include a selectable signal button to allow the user to select which signal will be transmitted or to vary the output signal automatically over desired time periods.

In one embodiment, the device further includes a microphone and a signal processor configured to receive a signal generated by the user's speech. In this embodiment, the device can then automatically output the auditory stimulus speech signal to the user based on an analysis of a received signal associated with the user's speech, such that the auditory stimulus speech signal is provided substantially contemporaneously with the user's speech independent of (without) auditory feedback or manipulation of the user's contemporaneous speech itself. Advantageously, the auditory stimulus speech signal is delivered in a manner which allows the user to speak at a substantially normal speech pace.

The device can also be configured to identify the initiation of speech production on the part of the user and the termination of speech by the user by monitoring the signal received by the microphone and signal processor. The device can substantially continuously or intermittently output the auditory stimulus speech signal while the user is speaking (such as concurrent with or during the speech of the user).

In one embodiment, the device can also include a detector operably associated with the processor and receiver (microphone). The detector is configured to detect the onset of or an actual stuttering event, and, in operation, upon recognition of the initiation of an impending or actual stuttering event on the part of the user, the device can output the auditory stimulus speech signal to the user.

As noted above, the auditory stimulus speech signal can comprise a plurality of different natural speech prolonged sounds associated with voice gestures which are independent of the contemporaneous speech of the user and can be configured to be serially output to the user.

Advantageously, the exogenously generated or second spoken speech signal is a vocal communication, utterance, or speech sound(s) which is incongruent with the speech production of the stutterer/user. The present invention, thus, provides an auditory stimulus which can be an effective acoustic mechanism to enhance the fluency in persons who stutter while also allowing users to speak at a substantially normal pace and without requiring the use of DAF or MAF. The second stimulus speech signal can be meaningful or not meaningful and can be presented in incongruent text or spoken speech at normal or stuttered fluency or in steady state spoken speech signals having appropriate duration or prolonged or sustained voice gesture sounds.

The foregoing and other objects and aspects of the present invention are explained in detail in the specification set forth below.

DESCRIPTION OF PREFERRED EMBODIMENTS

The present invention will now be described more fully hereinafter with reference to the accompanying figures, in which preferred embodiments of the invention are shown. This invention may, however, be embodied in many different forms and should not be construed as limited to the embodiments set forth herein.

Like numbers refer to like elements throughout. In the figures, layers, regions, or components may be exaggerated for clarity.

Figure 1:
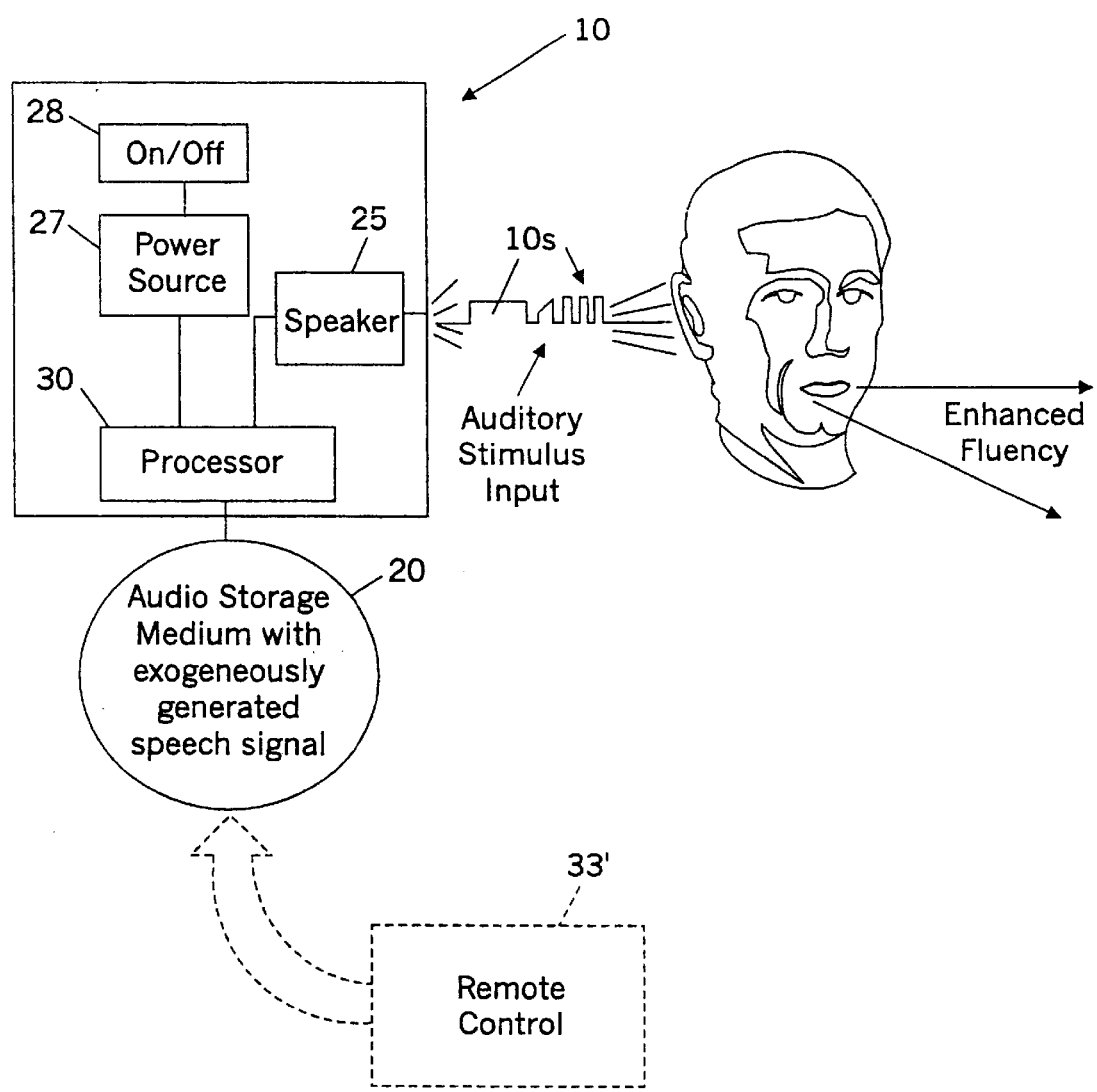
FIG. 1 is a schematic illustration of one embodiment of a device configured to transmit an exogenously generated natural speech signal as an auditory stimulus to a user according to the present invention.

As shown in FIG. 1, a device 10 is configured to provide an exogenously generated auditory (second) speech signal 10s to a speaker. As shown, the device 10 is preferably configured to transmit the speech signal 10s to the user temporally proximate in time to or, preferably, substantially contemporaneous with a speaking event (while the patient or user is speaking). As used herein, the term "exogenously" means generated by a cause external of the user, preferably by a person other than the patient/user, or, if generated by the user, that it is pre-recorded at a time in advance of use. It will be appreciated that the auditory stimulus of the instant invention does not require in situ manipulation or feedback of the user's contemporaneous speech and is incongruous with the content of the user's speech.

The exogenously generated speech signals of the present invention can be thought of as "second" speech signals, wherein the first speech signal is typically associated with the actual speech of the speaker. The instant invention, unlike many conventional stuttering devices and treatments, uses the second exogenously generated speech signal as an auditory stimulus. That is, the second speech signal is a natural or spoken speech signal (a voice gesture associated with a vocal cord) not contemporaneously generated by or associated with the contemporaneous speech of the speaker himself/herself. The second speech signal is also not configured to interrupt (or delay or mask or otherwise feedback) the actual contemporaneously uttered speech of the user. Thus, the second speech signal of the present invention is independent and separate from the contemporaneous speech of the user and is provided as an auditory stimulus to allow the user to speak at a substantially normal pace with enhanced fluency. The second natural speech signal can be coherent or incoherent (i.e., the second exogenously generated natural speech signal can have comprehensible meaning to the user or it can have no meaning to the user, rather, the natural speech signal can be a voice gesture or a collection of voice gestures). In one embodiment, the second speech signal is provided to the patient/user such that it is in the same language as that of the primary language of the user. Alternatively, the second speech signal can be generated by speech spoken in a language which is different from the primary language of the user.

Figure 2:
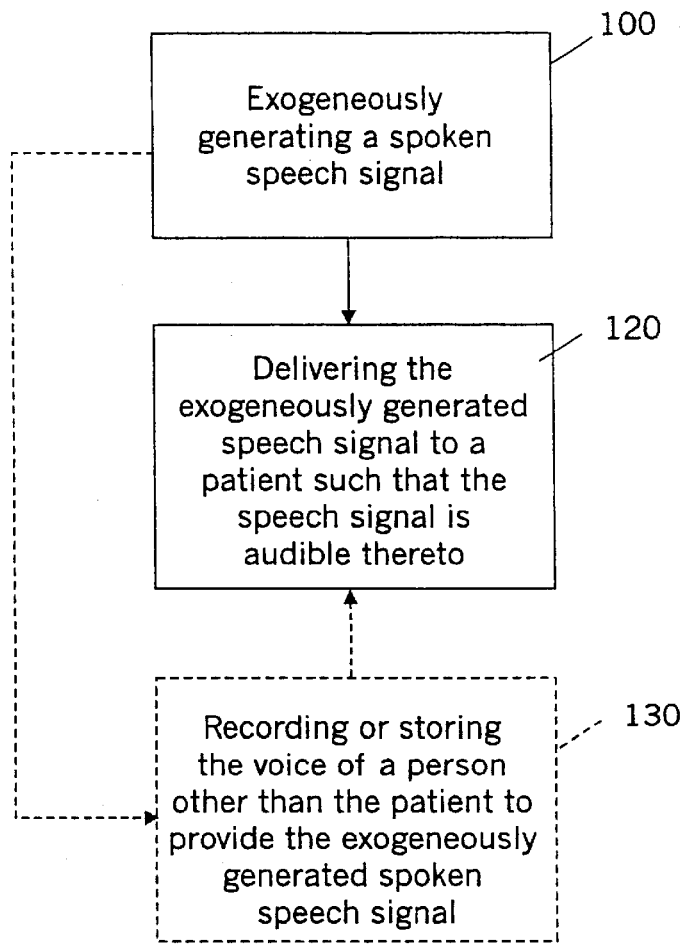
FIG. 2 is a block diagram of steps of one method for enhancing the fluency of a person who stutters according to the present invention.

FIG. 2 illustrates a method for enhancing the fluency of persons who stutter according to an embodiment of the present invention. The method comprises the steps of (a) exogenously generating a second speech signal (Block 100); and (b) delivering the exogenously generated speech signal to a patient (during and/or proximate to the speech production of the patient) such that the second speech signal is audible thereto (during or proximate) the patient's speech production) (Block 120).

In one embodiment, the method also optionally comprises the step of recording or storing the voice of a person other than the patient to provide the exogenously generated second speech signal (Block 130). The recording or storing of the second speech signal is done in a manner which will allow the second speech signal to be reconstructed or played and transmitted repeatedly to the patient or user at the appropriate or desired times. In this way, the patient has a reliable speaking aid to assist in fluency whenever the need arises.

The second or exogenously generated speech signal can be either stuttered or fluent. The second speech signal can comprise a prolonged voice gesture or vocal spoken sound such as a prolonged single vowel or consonant or a combination of vowels and/or consonants, either alone, or in combination, as will be discussed further below. Further, the exogenous or second speech signal of the instant invention can be provided to the patient in an intermittent manner (such as with a 25–75% duty cycle, or combinations thereof) while the patient or user is speaking (i.e., such that it is intermittent during speech production on the part of the patient/user). Alternatively, the second speech signal can be provided such that the signal is sustained for a period of time, or such that the speech signal is substantially continuously transmitted to the user during speech production. Preferably, the second signal is delivered to the user such that it is either continuous with activation of the device, with the speech production of the user/patient, or with the onset or during a stuttering episode of the user/patient. The second speech signal 10s can also be provided both in advance of (and temporally proximate to) the output of speech as well as substantially continuously or intermittently while the speaker/user is speaking.

As noted above, it is preferred that the second or exogenously generated auditory speech signal is generated by someone other than the user or stutterer. The second speech signal may be able to be generated by a device, such as an elongated tube, which is configured so as to substantially replicate a voice or vocal tract or cord associated with the voice gesture sound of a person, so that, in operation, the replicated voiced speech signal can trigger the auditory cortex of the stutterer/user. Of course, the stutterer can record the appropriate (pre-determined and incongruous) prolonged second speech signal(s) in advance of use for later playback for use as the second speech signal. However, it may be more economical to "burn" or record large quantities of standardized second speech signals suitable for a wide audience. Thus, it is also preferred that the voiced base speech signal of the instant invention be generated and saved (recorded, "burned", and/or stored) in advance of use such that it can be conveniently and reliably played or output at desirable times.

It is also preferred that the exogenously generated second speech signal of the present invention is generated to include a prolonged spoken voice gesture (emphasizing a selected spoken sound). It is more preferred that the second speech signal include at least one spoken prolonged syllabic sound (such as the last sound in the word "sudden") or a sonorant or continuant sound. As used herein the term "prolonged" means to emphasize or sustain the voice gesture sound over normal speech patterns, and preferably means to sustain the voice gesture in substantially steady state form for about at least 2–30 seconds. It is even more preferred that the second speech signal includes a spoken simple sustained or steady state vowel in whatever appropriate language (whether a Romance language or other human spoken language). For example, in the English language, a simple sustained /a/, /i/, /e/, /o/, /u/, and /y/.

In another embodiment, the exogenously voiced speech signal includes trains of vowels such as a three-vowel train. For example, in the English language, a three vowel train representing the three corner of the vowel triangle /a-i-u/ or other vowel trains or serially uttered sustained vowel sounds. Similarly, the second speech signal can include consonant trains or serially uttered (preferably prolonged or sustained) consonant and/or vowels or combinations thereof or sonorant or continuant sounds. Preferably, the second speech signal is delivered to the user or stutterer such that it has a sustained duration of at least between about 5 seconds 2 minutes. More preferably, the second speech signal is transmitted such that it has a duration which is at least about 5–10 seconds and provided, as needed or desired, every 10–30 seconds to every 1–2 minutes (which can be repeated at the same time intervals or can be intermittently transmitted closer and further apart in time) during ongoing speech production such that the signal is relayed to the user intermittently throughout the speech production on the part of the user. It should also be noted that the second speech signal can be recorded as a single short signal (such as about a 1–5 second signal) which can then be looped to provide a longer length output second speech signal. For example, an exogenously generated speech signal having a 1 second (in duration) length can be electronically (such as by digital or analog means) looped 10 times to output a 10 second signal to the user.

The output or transmission of the second speech signal can be varied and/or timed or controlled by a timer incorporated into the device which times the transmission output of the second signal (such as based on the activation of the device or from the initially transmitted or output second speech signal). However, as noted above, the second speech signal can be otherwise provided such as substantially continuously (typically substantially overlapping with the duration of the speech production itself) or intermittently throughout (or provided as needed or desired during or proximate to) speech production of the user or patient responsive to the needs of the user. As such, the exogenously generated speech signal of the present invention can be provided just prior to or at the start of speech production of a speaker prone to stuttering and/or episodically during speech, such as when a person starts to stutter or is experiencing a stuttering event (either of which can be provided in several ways such as via a user input or activation button on the device). The device can also have a selectable duty cycle or timing function input to allow a user to select or vary the desired duration or output transmission cycle (not shown).

In one embodiment, the second speech signal can be provided as an arrangement of different spoken or voice gesture sounds to alter the exogenous voiced speech stimulus to the user, over time. For example, the enhanced fluency treatment can be performed by providing a first exogenous speech signal comprising a sustained steady state /a/ voice gesture sound (preferably relayed to the user proximate in time to either the start of speech production or for a first stuttering event) followed by a second different exogenous speech signal comprising a sustained /e/ (preferably for a subsequent stuttering event or perhaps a second speaking event or speech production temporally spaced apart from the start of the first speech production event or for a different speaking period), followed by the first exogenous signal (repeated) or a third different exogenous signal such as another sustained substantially steady state vowel or vowel train or a sustained consonant, and the like.

The methods and devices of the present invention may also provide exogenously generated second speech signals with a mixture of selectable natural speech signals, some of which may provide improved results for a particular type of stuttering disorder or for particular users as well as for other communicative disorders. For example, one may record the exogenously generated or second speech signals onto a compact disk (or tape) having multiple sound tracks, each providing a different second speech signal (different spoken utterances or voice gestures) relative to the others. Alternatively, a changeable storage medium such as an audio chip or DSP unit, and the like, can be used to provide selectable or changeable second speech signal and thus, selectable or changeable auditory stimulus.

Turning again to FIG. 1, the present invention includes devices 10 which are configured, in operation, to provide, relay, or transmit a pre-recorded or stored second speech signal 10s to the patient. The second speech signal 10s is preferably exogenously generated by a person other than the user. As shown in FIG. 1, the device 10 preferably includes at least one speaker 25, a power source 27, and a speech or audio signal storage medium 20. Preferably, as shown in FIG. 1, the device 10 also includes an user-accessible on/off activation switch 28 to allow the power source 27 (such as a battery) to be disconnected during periods of non-use, thereby preserving battery life (when the device is not wired and connected to an electrical outlet). The speech signal storage medium 20 is operably associated with the speaker and the power source 27 such that the device 10 is able to output the second speech signal upon activation thereof. Optionally, the device 10 can be activated and/or various parameter of the speech signal 10s output adjusted (such as its volume, signal duration or length, signal sound type, and the like) by a remote control unit 33'.

The speech signal 10s can be captured and held by any number of suitable speech signal storage media 20, including, as non-limiting examples, processor circuits including digital signal processors such as DSP chips, audio cards, sound chips, general purpose computers, compact disks, tapes, computer program products (including those downloadable from an internet site), or other sound recording or audio storage mediums.

Figure 3:
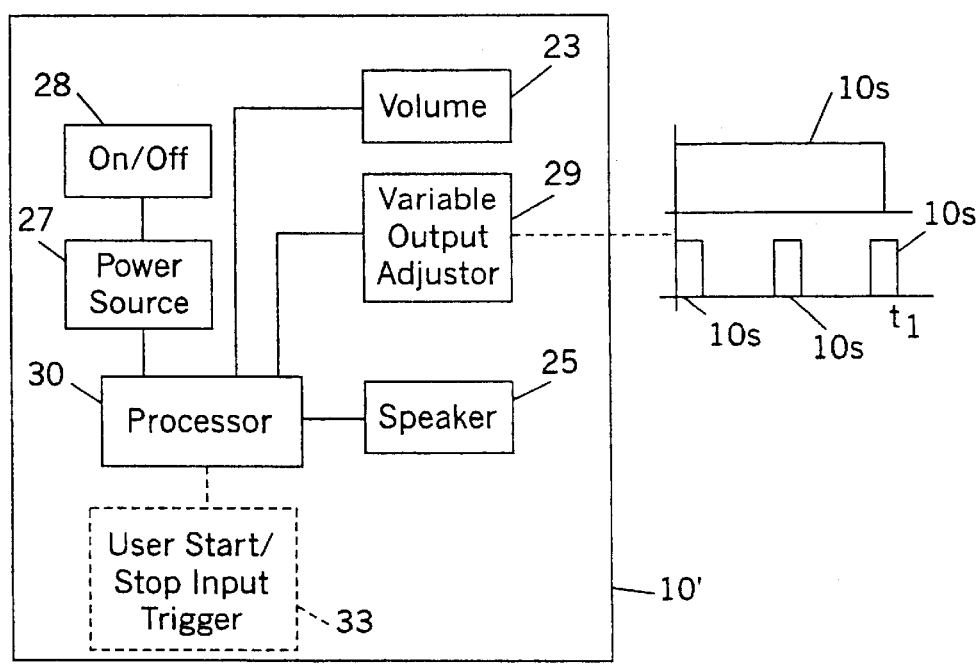
FIG. 3 is a schematic illustration of another embodiment of a device according to the present invention.

FIG. 3 illustrates another embodiment of the present invention. As shown, the device 10' includes a processor 30 which is operably associated with the speaker 25. The processor 30 can be an analog or digital signal processor and is preferably a microprocessor such as a DSP. The processor 30 is configured to provide the speech signal 10s to the speaker 25 such that it is audible to the user. As shown, the device 10' can also include a user start/stop trigger switch 33 which is configured to allow the user to generate a substantially immediate output (or termination) of the speech signal 10s. As is also shown, the device 10' can include a volume control 23 and/or a variable signal output adjustor 29 to allow a user to adjust the output of the signal 10s to his or her needs. That is, as shown connected to the adjustor 29 in dotted line, in one embodiment, the user can increase or decrease the duration or frequency of the transmitted second speech signal 10s from a continuum ranging from continuously outputting the signal during speech production or a desired output time ($t_1$) period to intermittently outputting the signal at desired adjustable intervals during the desired output period ($t_1$).

Figure 4:
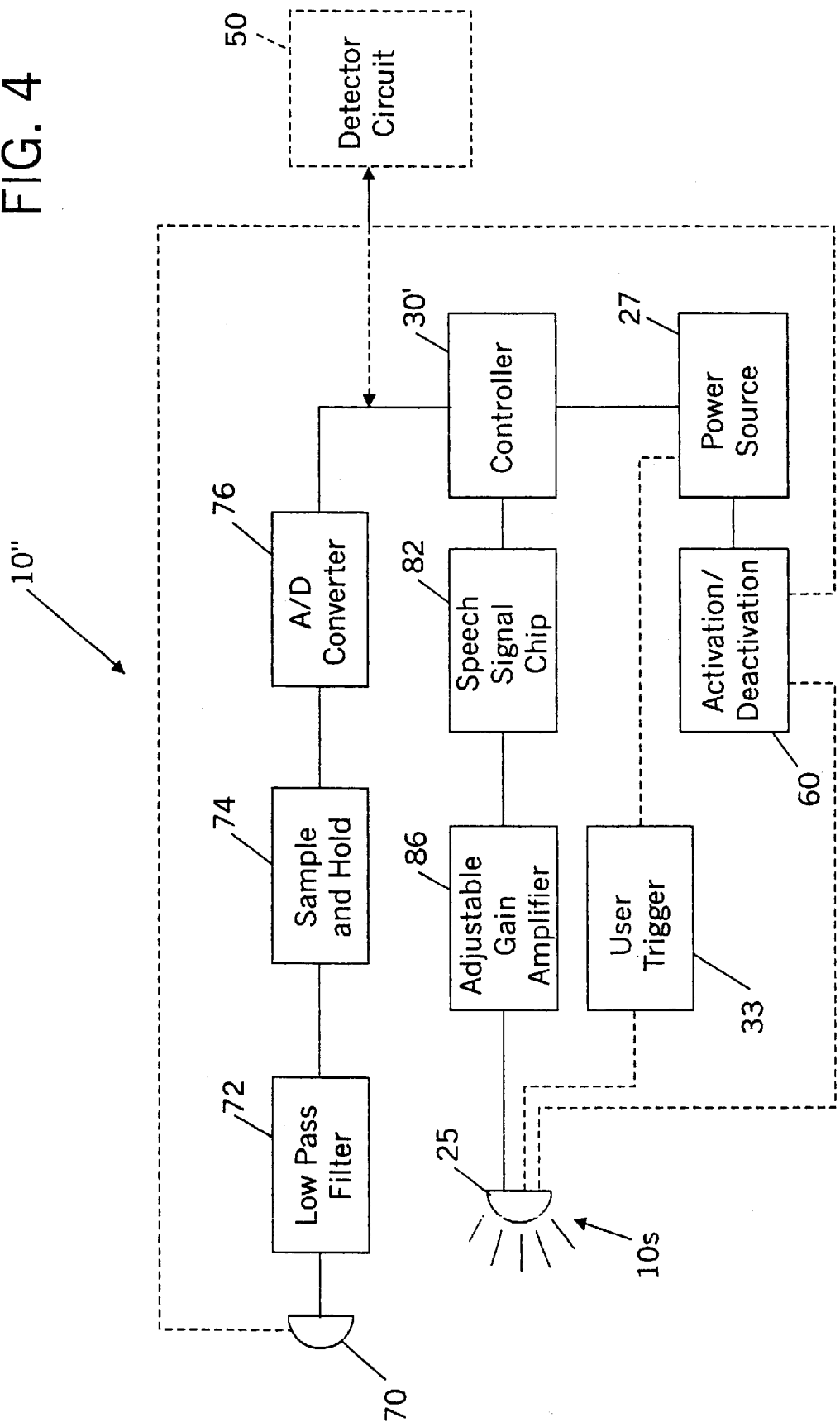
FIG. 4 is a schematic illustration of an additional embodiment of a device according to the present invention.
Figure 5A:
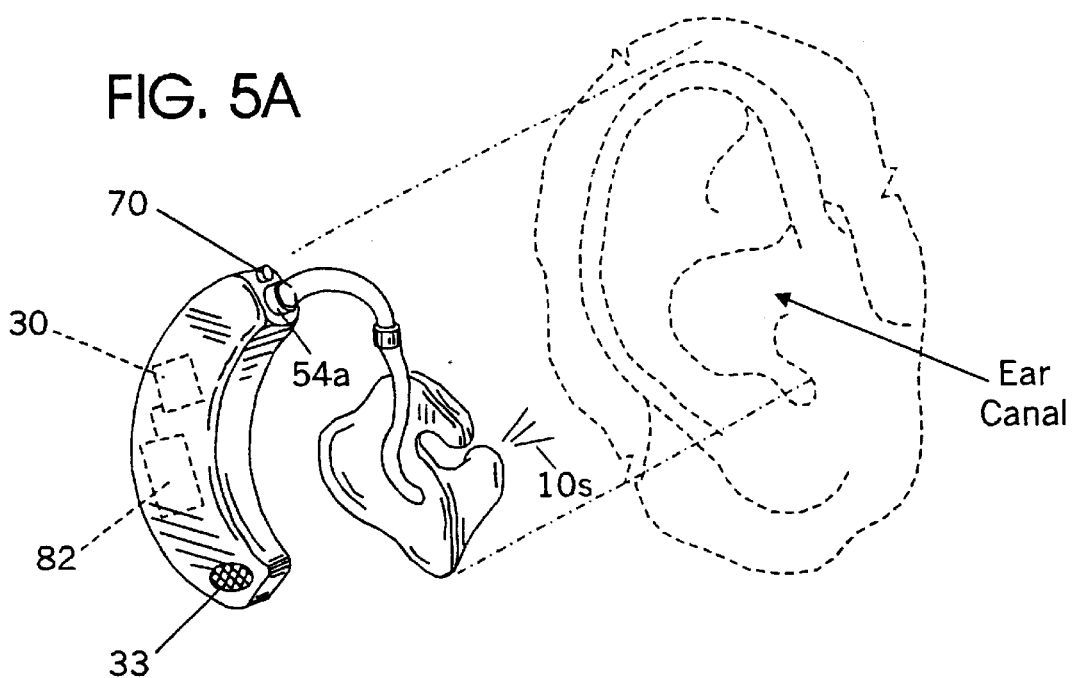
FIG. 5A is a side perspective view of a behind-the-ear (BTE) device according to one embodiment of the present invention.
Figure 5B:
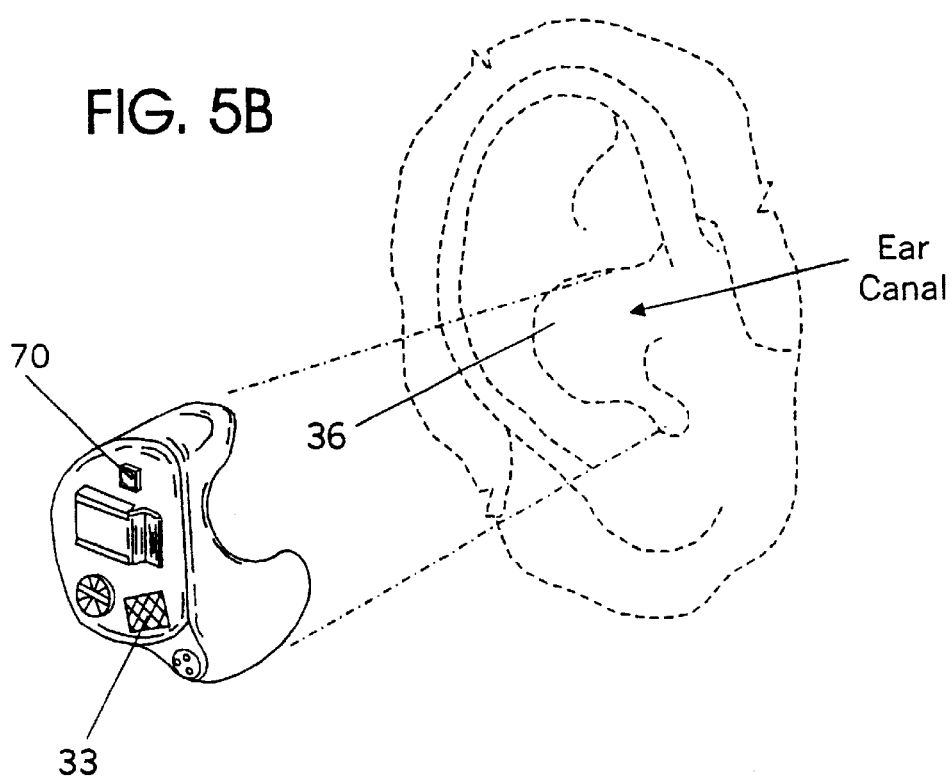
FIG. 5B is a side perspective view of an in-the-ear (ITE) device according to one embodiment of to the present invention.

FIG. 4 illustrates an additional embodiment of the present invention. In this embodiment, the device 10" is configured to monitor at least portions of a user's speech so as to be able to identify the initiation and termination of speech (and thus the duration of a speaking event) of the user. The device 10" can use this information to automatically deliver the speech signal 10s concurrently with a user's speaking, without requiring the user manually activate the device 10". Alternatively, the device 10" can include a detector circuit 50 to detect the onset or occurrence of a stuttering event to transmit the speech signal 10s responsive to a detected episodic stuttering event. Of course, the device 10" can additionally employ a user trigger 33 which can be manually activated. Preferably, the device 10" is configured as one of an OTE, BTE, or ITE device (such as shown in FIGS. 5A and 5B). Other details of typical elements of suitable compact portable devices and descriptions thereof are described in U.S. Pat. No. 5,961,443 to Rastatter et al.

As shown in FIG. 4, the device 10" comprises a receiver 70 such as a microphone or transducer configured to receive the sound waves associated with the speech production of the user during operation. The receiver 70 produces an analog input signal of sound corresponding to the user's speech. Preferably, as shown in FIG. 4, the analog input signal is converted to a stream of digital input signals for subsequent analysis. In one embodiment, the device 10" includes a low pass filter 72 to inhibit aliasing. The low pass filter 72 is located after the receiver 70 and before an A/D converter 76. The cutoff frequency for the low pass filter 72 is preferably sufficient to reproduce a recognizable voice sample after digitalization. A conventional cutoff frequency for voice is about 8kHz. Filtering higher frequencies may also remove undesirable background noise.

The output of the low pass filter 72 can be input into a sample and hold circuit 74. As is well known in the art, the sampling rate should exceed twice the cutoff frequency of the low pass filter 72 to reduce the likelihood of introducing sampling errors. The sampled signals output by the sample and hold circuit 74 are then input into the A/D converter 76. The digital signal stream representing a desired sampling of data sufficient to allow the device 10" to determine that the user has commenced or terminated speech production is then fed into a controller 30' which is configured to analyze the digital stream to determine whether speech production has been initiated, or terminated or is continuing.

As shown, the controller 30' is in communication with the power source 27 and the speaker 25. In this embodiment, the device 10" also includes a speech signal chip 82 which stores the recorded audio second speech signal 10s. Of course, the controller 30' can be a DSP or other signal processor which can itself hold or store the audio speech signal therein. That is, the speech signal chip 82 does not need to be a separate component, but is merely illustrated as such for ease of description in the figures. The device 10" can also include an adjustable gain amplifier 86 to adjust the output of the signal 10s to a desired comfortable listening level.

During operation, the controller 30' analyzes the digital stream associated with the input signal from the receiver 70 to determine if the user has initiated speech (typically indicated by the analog or digital voice signal rising above a predetermined threshold level). If so, the controller 30' can proceed to automatically power the speaker 25 and output the speech signal 10s to the speaker 25. The controller 30' can continue to monitor samples of the digital stream to determine if speech is continuing to thereby continue to activate the speech signal. As noted above, the speech signal can be output intermittently during speech or substantially continuously with speech. Once the controller 30' determines that speech has terminated, the speech signal 10s can also be automatically terminated.

As is also shown in FIG. 4, the device 10" may include an activation/deactivation circuit 60 which is configured to interrupt transmission from the receiver 70 (such as a microphone) to the earphone or speaker 25. One embodiment of such a circuit is described in U.S. Pat. No. 4,464,119 to Vildgrube et al., the contents of which are hereby incorporated by reference as if recited in full herein. Thus, the device 10" can be configured so that it can be interrupted either manually and/or automatically by switching the power off or to "standby" when the user's speech production falls below a predetermined threshold level.

In one embodiment, the device 10" can include a stuttering detector circuit 50. This detector circuit 50 is associated with the controller 30' and the digital data stream corresponding to the user's speech. The detector circuit 50 is configured such that during operation it identifies an irregular speech production pattern which can cause the controller 30' to immediately transmit the speech signal 10s to the user to enhance fluency. The device 10" may also increase the volume of the signal if a second speech signal is already being transmitted to the user, or may vary the speech signal transmitted to the user to a different second speech signal, as described above. Typical irregular speech patterns can be identified by prolongation of sounds (corresponding to part word or word prolongation), repetition of sounds (corresponding to part-word or word repetitions), and the like. Although shown as a separate circuit from the controller 30', the detector circuit 50 can also be incorporated into the controller 30' itself (as hardware, software or a combination of same). Examples of suitable means for identifying stuttering events are described in the following references: Howell et al., *Development of a two-stage procedure for the automatic recognition of dysfluencies in the speech of children who stutter*: II. *ANN recognition of repetitions and prolongations with supplied word segment markers*, Journal of Speech, Language, & Hearing Research. 40(5):1085–96, (October, 1997); Howell et al., *Development of a two-stage procedure for the automatic recognition of dysfluencies in the speech of children who stutter: I. Psychometric procedures appropriate for selection of training material for lexical dysfluency classifiers*, Journal of Speech, Language, & Hearing Research, 40(5):1073–84, (October, 1997); Howell, et al, *Automatic recognition of repetitions and prolongations in stuttered speech*, C. W. Starkweather and H. F. M. Peters (Eds), Proceedings of the First World Congress on Fluency Disorders, Vol. II (pp. 372–374), Nijmegen, The Netherlands: University Press Nijmegen. (1995); and Howell et al., *Automatic stuttering frequency counts*, W. Hulstijn, H. Peters and P. Van Lieshout (Eds.), Speech Production: Motor Control, Brain Research and Fluency Disorders, Amsterdam: Elsevier Science, 395–404 (1997). The contents of these references are hereby incorporated by reference as if recited in full herein.

Figure 6:
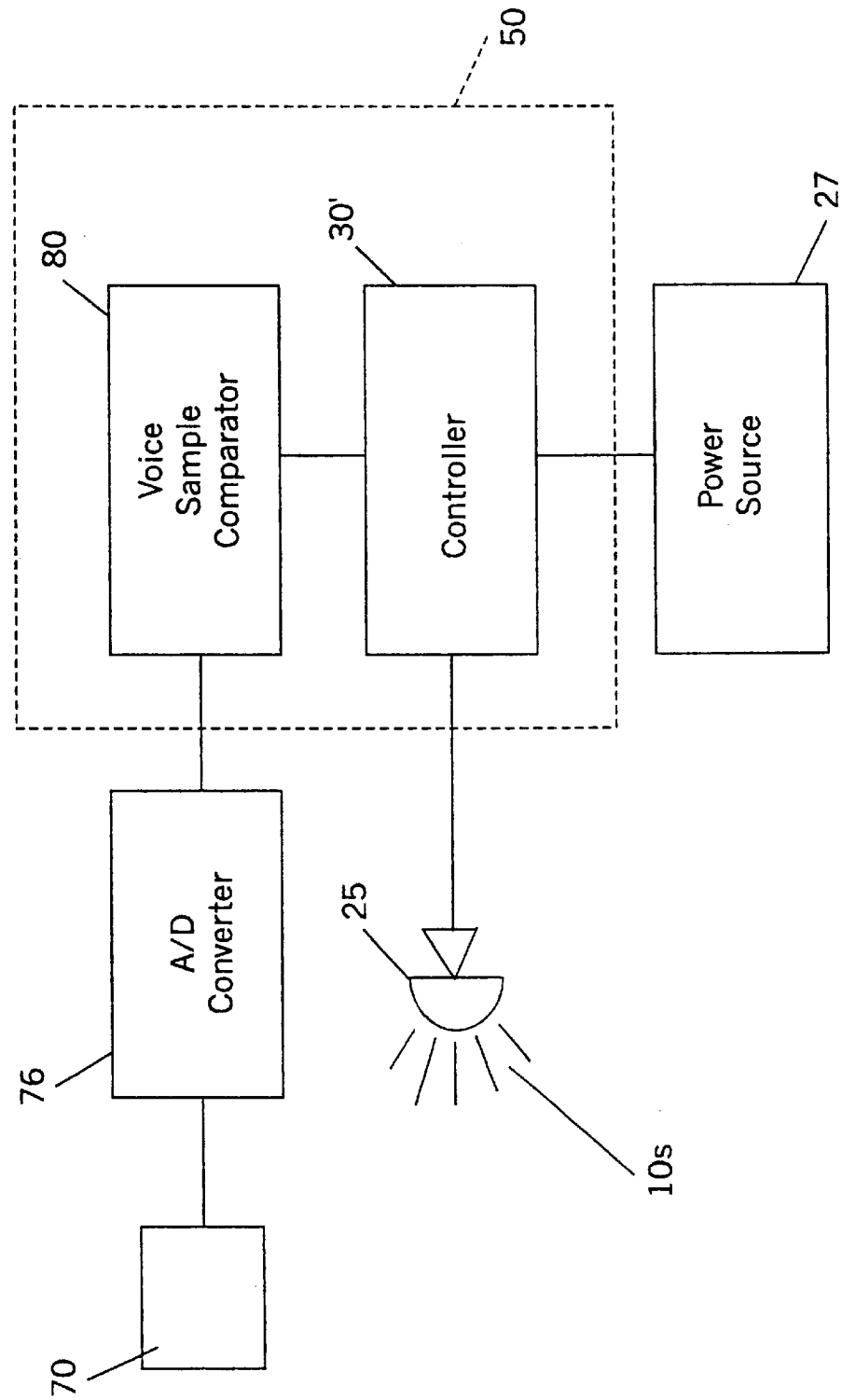
FIG. 6 is a schematic illustration of another embodiment of a device according to the present invention.

FIG. 6 illustrates one embodiment of a detector circuit 50 which employs a voice comparator 80 to compare speech patterns of the user to identify irregular speech patterns associated with the onset or occurrence (or termination) of a stuttering event. The voice comparator 80 is configured to compare fluent or normal voice signals to irregular or stuttered voice signals to identify the presence of a stuttering event.

As discussed above, the second speech signal can be held in and delivered by portable miniaturized devices such as ITE (in the ear), BTE (behind the ear) or OTE (over the ear) stuttering aid devices such as shown in FIGS. 5A and 5B. The devices can be configured as either a monaural or binaural input device to the user (residing in or proximate to a single or both ears).

Alternatively, the auditory speech based stimulus of the instant invention can provided in a number of ways. In some embodiments, the audio stimulus can be generated from standalone handheld or wearable devices or provided as a compact disk (FIG. 7C) or audiotape, or downloadable computer program code (such as transmitted from a global computer network system), or other computer readable program formats code. The first type can be can be output by typical tape players and CD players while the latter type can be played or output by a general purpose . (FIG. 7G), laptop, or miniaturized, handheld, palm, or wearable computers.

Recently, consumer electronics companies have proposed wearable devices (featuring a body area network) on a jacket. This device also includes a headset which can allow a user to listen to a phone call and music using the same headphone or headset and is configured to allow a user to switch between the two modes with a remote control switching device. This technology may be suitable to integrate the second speech signal of the present invention into a similar device so as to be output as an alternative to or in addition to the outputs now allowed, music, second speech signal, and listening to a phone call. Thus, the second speech signal can be output from the headset upon activation of the output via a remote control unit in order to relay and output the second speech signal into the headset while the user is listening to a phone call via the same headset. See e.g., *New Wired Clothing Comes With Personal Network*, cnn.com/2000/TECH/computing/8/18/wired jacket.idg/index.html (posted on Aug. 18, 2000). The content of this document is hereby incorporated by reference as if recited in full herein.

Figure 7A:
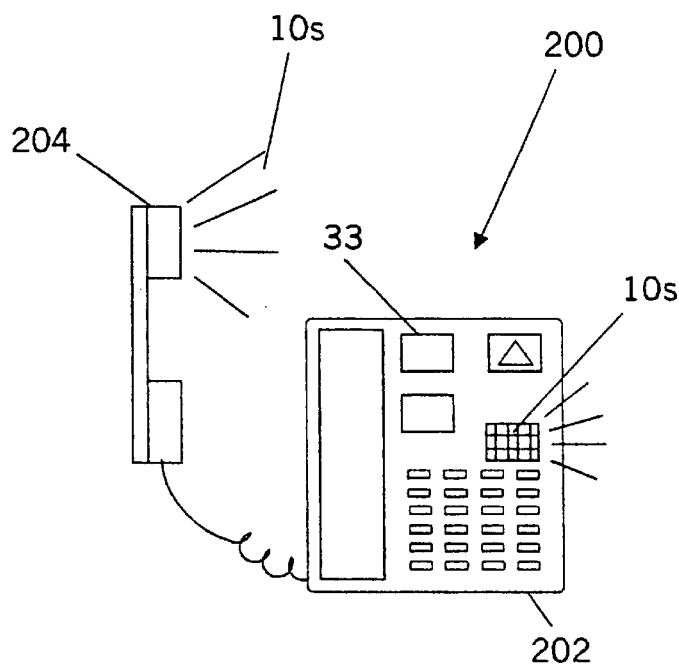
FIGS. 7A–7G illustrate exemplary embodiments of devices which can transmit an exogenously second speech signal according to the present invention.
Figure 7B:
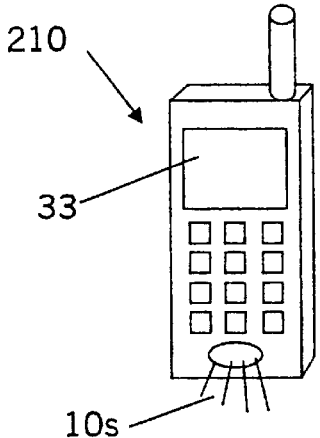

Alternatively, the second speech signal audio-stimulus of the present invention can be incorporated into conventional consumer devices. For example, it is anticipated that the audio natural speech signal stimulus of the present invention can be incorporated into communication devices having voice or microphone inputs (such as the handset or base of a telephone or wireless telephone body) or other audio-prompter devices which can be easily accessed and used when a user will be typically expected to speak at various times during operation. FIG. 7A illustrates that the second speech signal 10s can be transmitted from one or more of the base 204 or handset 202 of a telephone 200. FIG. 7B illustrates that the signal 10s can be transmitted from a wireless telephone body 210.

Figure 7C:
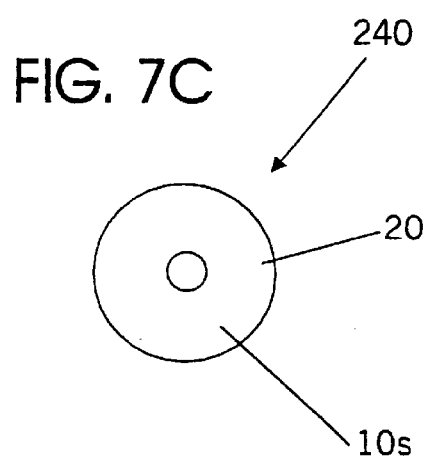
Figure 7D:
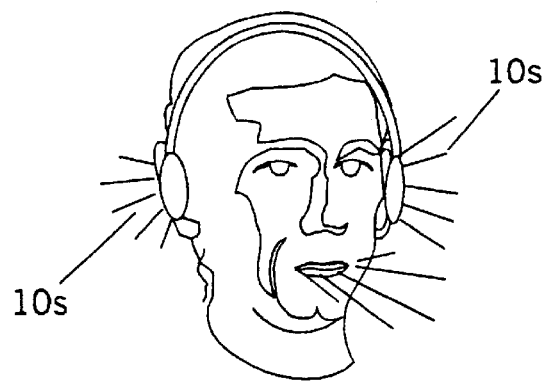
Figure 7E:
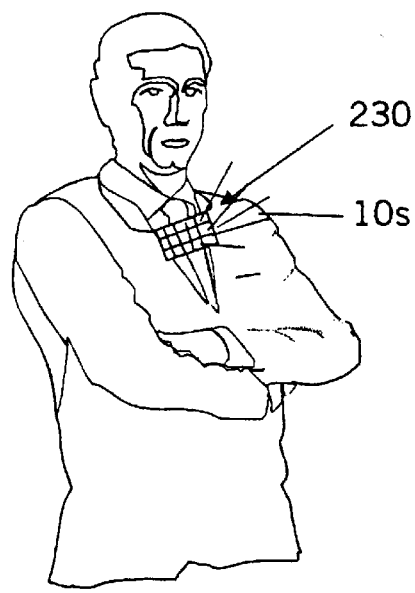
Figure 7F:
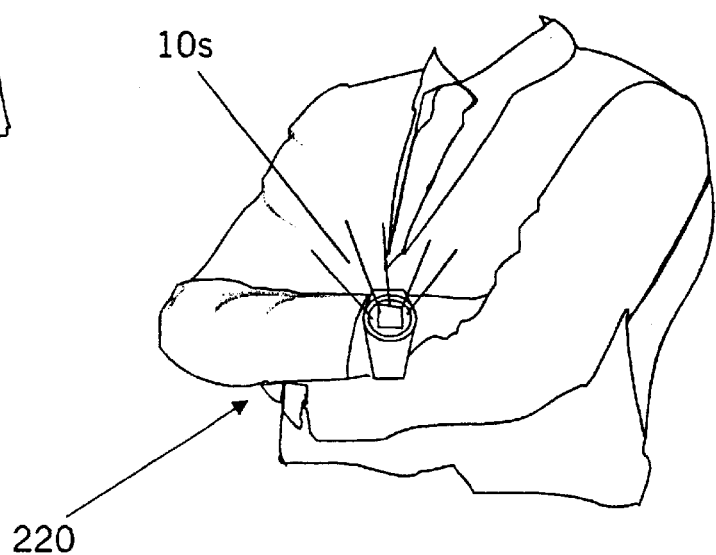
Figure 7G:
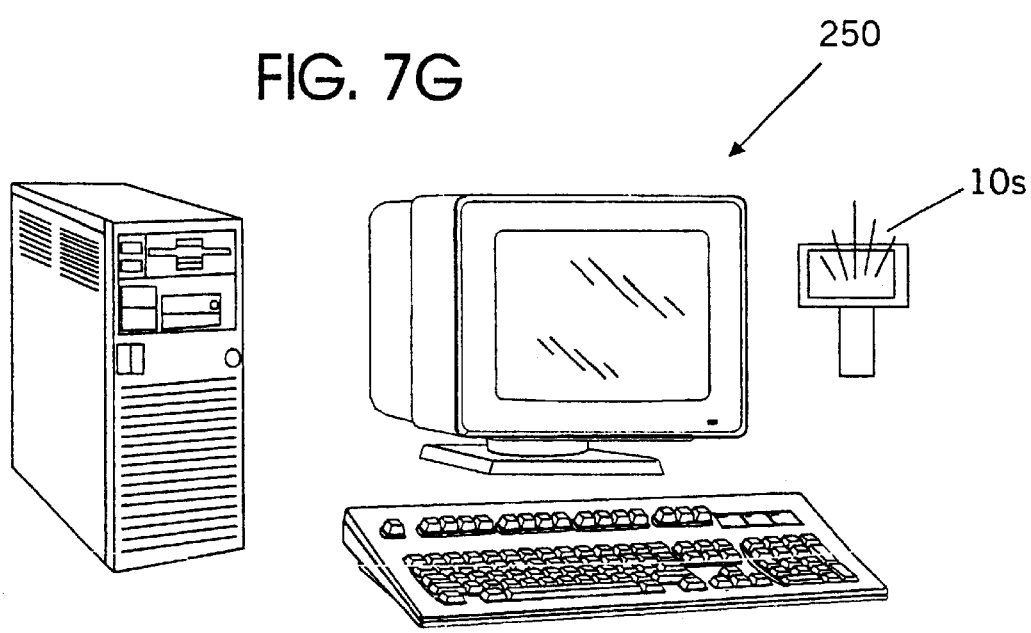

In other embodiments, the second speech signal 10s can be held in and provided by (wrist or other type) watches 220 (FIG. 7F), bracelets, lapel or shirt pins, necklaces 230 (FIG. 7E) or other proximately worn (within the audible range of the user or patient) jewelry, headbands, eyeglass frames, hats, and the like. FIG. 7D illustrates a headphone device configured to provide a binaurally relayed second speech signal 10s which as shown is output from earphones 240. FIG. 7C illustrates a compact disk or other audio storage media 240 while FIG. 7D illustrates a computer 250 with audio output. In any event, the exogenously generated auditory stimulus associated with the instant invention can be an effective acoustic mechanism to enhance the fluency in persons who stutter.

Some embodiments of the devices 10, 10', 10" of the present invention may employ external battery packs while others may employ internal battery power sources. Of course, extension cords and direct power cords and trickle chargers can also be employed. One example of a known BTE hearing aid with DSP and an external battery and processing pack is the PHOENIX produced by NICOLET Company of Madison, Wis.

As will be appreciated by one of skill in the art, the present invention may be embodied as methods, devices or computer executable programs. Accordingly, the present invention may take the form of a hardware embodiment or an embodiment combining software and hardware aspects.

The present invention is also described using flowchart illustrations and block diagrams. It will be understood that each block (of the flowchart illustrations and block diagrams), and combinations of blocks, can be implemented by computer program instructions. These program instructions may be provided to a processor circuit(s) within the mobile user terminal or system, such that the instructions which execute on the processor circuit(s) create means for implementing the functions specified in the block or blocks. The computer program instructions may be executed by the processor circuit(s) to cause a series of operational steps to be performed by the processor circuit(s) to produce a computer implemented process such that the instructions which execute on the processor circuit(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

EXAMPLES

Exogenous stuttered and normal speech signals were generated and compared for effectiveness. Incongruent speech signals were used in order to compare the inherently incongruent nature of exogenous stuttered speech to that of incongruent fluent speech (in incongruent speech, the second speech signal contains different phonemic material than that read aloud by the participants) to determine if fluency reduction is achieved and what components of the incongruent second speech signal might be responsible for the reduction in stuttering (or the enhancement in fluency). Thus, the natural classification scheme of vowels and consonants were examined in both dynamic and relatively static vocal tract positions. Experiment I involved meaningful speech: normal continuous speech, normal interrupted speech, stuttered continuous speech, and stuttered interrupted speech. Experiment II involved vowels and consonants: /a/, /a-i-u/, /s/, /s-sh-f/.

Ten normal-hearing adults who stutter (8 males, 2 females, mean age 27.9 years, SD 9.4) participated in both experiments. Participants did not present with any other speech and language disorders. All participants had a history of therapy but were currently not receiving any formal therapeutic intervention. Participants read different junior high-level passages of 300 syllables with similar theme and syntactic complexity in both experiments. The two experiments were counterbalanced while the experimental conditions and the passages were randomized. The participants were instructed throughout the experiment to read at a normal rate and not to use any controls to reduce or inhibit stuttering. In both experiments, participants listened to auditory feedback via supra-aural earphones at a comfortable listening level.

The first experiment required participants to listen to incongruous fluent or stuttered speech samples presented continuously or intermittently (50% duty cycle). Both speech samples were incongruent recorded text. The stuttered speech sample contained discrete stuttering acts on all words.

In the second experiment, participants listened to four continuous speech signals: a steady state neutral vowel /a/; a three vowel train representing the three corner of the vowel triangle /a-i-u/; a steady state consonant /s/; and a three consonant train /s-sh-f/. The consonants were selected as these could be presented in the absence of a vowel. Steady vowels and consonants and trains of each were used to represent different levels of proximity with the speech act. Participants also read a control passage with Non-altered Auditory Feedback (NAF). Stuttering episodes were calculated from the participants' videotape recorded passages. Stuttering was defined as part-word repetitions, part-word prolongations, and/or inaudible postural fixations.

The stimuli for these samples were recorded in a sound-treated room with a digital tape recorder (SONY model 8819). A normal fluent American English-speaking adult male produced the vowel, consonant, and fluent speech samples for both experiments. An American English speaking adult male who stutters produced the stuttered speech sample for the first experiment. Both speakers produced speech samples at normal vocal effort. The fluent speech samples used text at junior high level text passages with similar theme and syntactic complexity as those read by the participants of the experiments.

The recorded signals were then fed into a personal computer (Apple Power Macintosh 9600/300) via an APPLE sound input port. Sampling was performed at 44 kHz. Sound analysis software (SOUND EDIT version 2) was used to introduce silence, select the various stuttering moments, and loop the signals. Silent intervals randomly varied from two to five seconds. These were then recorded onto a compact disk that was used to deliver the signal via a compact disk player (SONY model CFD-S28). The signals were delivered binaurally via headphones (OPTIMUS model PRO.50MX) at an audible level comfortable to the participant. All participants spoke into a lapel microphone (RADIOSHACK model 33–3003) affixed at about 15 cm or less from their mouths with an approximate orientation of 0 azimuth and –120 altitude. The microphone output was fed into a video camera (SONY model CCD-TVR 75).

Figure 8:
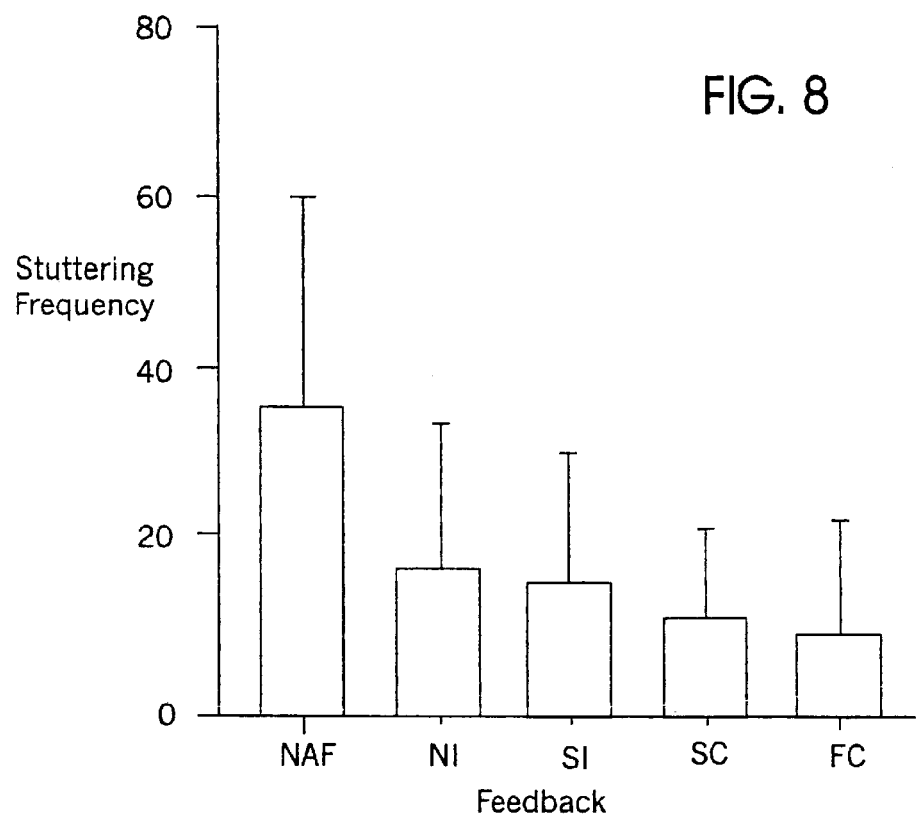
FIG. 8 is a graph of the results of an experiment illustrating mean stuttering frequency as a function of auditory feedback from a first experiment according to the present invention.

Mean stuttering frequency and standard errors for stuttering frequency as a function of auditory feedback condition for Experiment 1 is shown in FIG. 8, the error bars represent plus one standard error of the mean. In the figure, "NAF" represents non-altered auditory feedback, "FI" represents fluent interrupted, "SI" represents stuttered interrupted, "SC" stuttered continuous, and "FC" represents fluent continuous. As shown, a significant main effect of auditory feedback on stuttering frequency was found ($p=0.0004$). Single-df comparisons revealed there was a significant reduction in stuttering for all forms of altered auditory feedback relative to NAF ($p<0.0001$). No statistically significant differences were observed between fluent and stuttered speech feedback ($p=0.76$), or continuous and interrupted speech feedback ($p=0.10$).

Figure 9:
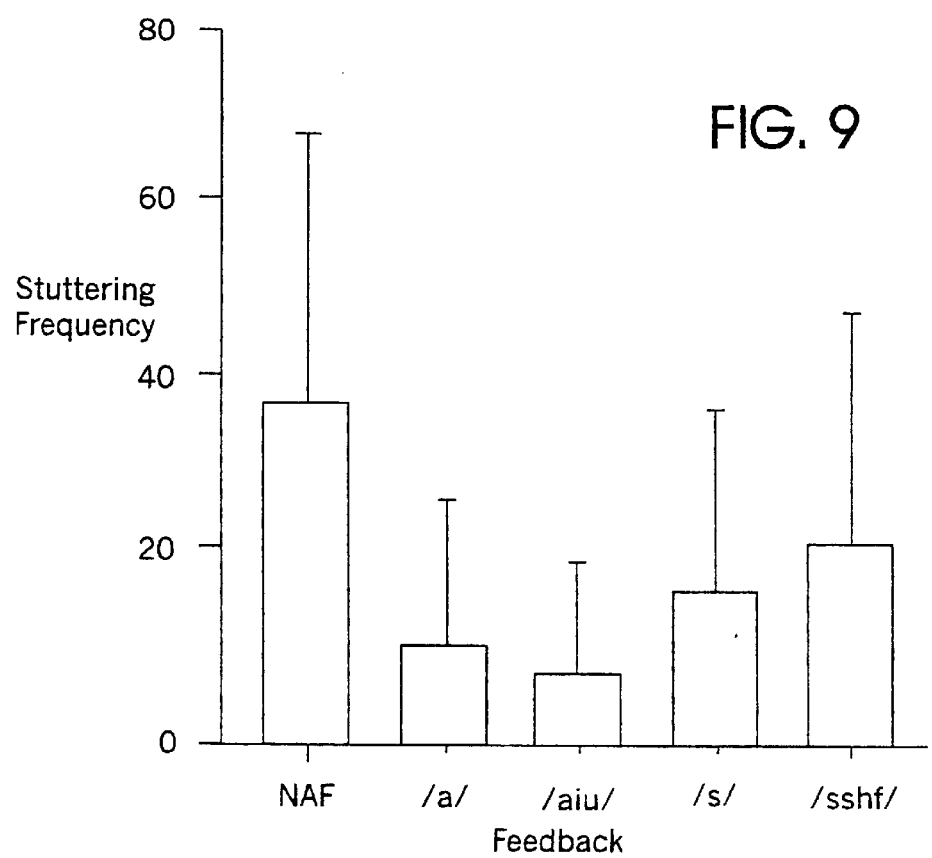
FIG. 9 is a graph of the results of a second experiment illustrating mean stuttering frequency as a function of auditory feedback according to the present invention.

Means and standard errors for stuttering frequency (i.e., the number of stuttering episodes/300 syllables) as a function of auditory feedback for Experiment II are shown in FIG. 9. Error bars represent plus one standard error of the mean. In FIG. 9, "NAF" represents non-altered auditory feedback. A significant main effect of auditory feedback on stuttering frequency was found ($p=0.0006$). A post hoc single-df comparison revealed there was a significant reduction in stuttering frequency for all forms of altered auditory feedback relative to NAF ($p<0.0001$). There were also statistically significant fewer stuttering episodes when the auditory feedback was a vowel or vowels versus consonants ($p<0.0001$). Non-significant differences in stuttering frequencies were found between single versus trains of speech components ($p<0.40$).

This set of experiments provides empirical documentation that an exogenously generated stuttered incongruous voiced or spoken speech signals can induce or increase fluency in persons who stutter. Indeed, the results indicate that stuttering frequency can be reduced irrespective of whether the exogenous signal is based on stuttered or normal speech. Further, the use of an exogenously generated voiced speech signal comprising vowels may provide improved efficacy in enhancing fluency in those who stutter.

In view of the foregoing, it appears that stuttering may be a natural compensatory mechanism to an "involuntary block" at a central level, rather than a peripheral manifested problem. Stated differently, the person stutters in an attempt to generate an auditory release mechanism for an "involuntary block" in speech execution at the central level. The overt manifestations of stuttering are an attempt to compensate at the peripheral level for a loss of control at the central level, albeit via a conspicuous compensation. Thus, stuttering is hypothesized to be a form of compensation rather than a problem in itself. Stuttering can be analogized to the role of a fever in an infectious disease state. The lack of an appropriate fluency enhancing gesture is hypothesized to be the predominate etiological factor that is exhibited or manifested due to a lack of inhibition on the part of the auditory cortex in assimilating the appropriate plan for smooth execution of the speech act. Recent brain imaging procedures have employed choral speech condition to induce fluent speech in adults who stutter and have compared the brain images obtained to those attained during stuttering events/behaviors. See, e.g., Fox et al., A PET *Study of the neural systems of stuttering*, 382 Nature pp. 158–161 (1996); Wu et al., *A positron emission tomograph [18$^F$]deoxyglucose study of developmental stuttering*, 6 Neuroreport pp. 501–505 (1995). A lack of activation in the auditory areas during the motor planning of stuttered speech was observed, but an essential normalization under the choral speech condition was noted, indicating fluency enhancing potential.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for enhancing the fluency of persons who stutter, comprising:

exogenously generating a speech signal of at least one prolonged voice gesture;

producing speech defining a first speech signal corresponding to the patient speaking, the patient having a propensity to stutter during speech production; and intermittently delivering the exogenously generated speech signal to the patient temporally proximate to said producing step such that the exogenously generated speech signal is audible thereto to thereby enhance the fluency of the patient.

2. A method according to claim 1, wherein the at least one prolonged voice gesture speech signal comprises a predetermined prolonged substantially steady vowel sound.

3. A method according to claim 1, wherein said delivering step is carried out in advance of and temporally proximate to said producing step.

4. A method according to claim 2, wherein the patient speaks at substantially normal speech speeds during said producing step.

5. A method according to claim 1, wherein said exogenously generated speech signal comprises a prolonged /a/ sound.

6. A method according to claim 5, wherein the prolonged /a/ sound is sustained for at least about 2 seconds.

7. A method according to claim 1, wherein said delivering step is provided before and then intermittently during said producing step.

8. A method according to claim 1, wherein said exogenously generated speech signal comprises a substantially continuant single syllabic vowel sound sustained for at least about 5 seconds.

9. A method according to claim 1, wherein said exogenously generated speech signal comprises a substantially continuant single consonant sound having a duration of at least about 5 seconds.

10. A method according to claim 1, wherein said exogenously generated speech signal comprises a plurality of prolonged predetermined voice gesture sounds spoken by a person other than the patient and electronically stored and reproduced using a portable device including at least one of (a) a prolonged vowel train sound and, (b) a prolonged vowel sound.

11. A method according to claim 10, wherein said exogenously generated speech signal comprises a plurality of said prolonged sounds serially delivered to the patient so that each is delivered temporally spaced apart from the other.

12. A method according to claim 1, further comprising the step of automatically detecting a stuttering event when the patient is speaking and initiating the delivery step upon the detection of the stuttering event.

13. A method according to claim 12, wherein said delivering step is automatically selectively carried out in response to said detecting step.

14. A method according to claim 1, wherein said delivering step is carried out responsive to user input to initiate said delivering step.

15. A method according to claim 1, further comprising the step of storing in an audio medium the exogenously generated signal, wherein said exogenously generated speech signal is provided by a spoken voice from a person other than the patient.

16. A method according to claim 15, wherein said delivering step is carried out by transmitting the stored exogenously generated speech signal.

17. A method according to claim 16, wherein said delivering step is repeated a plurality of times during said producing step.

18. A method according to claim 15, wherein said exogenously generated speech signal comprises a plurality of different spoken prolonged voice gesture sounds, each having a sustained duration which is at least about 10 seconds long.

19. A method according to claim 1, wherein said delivering step is carried out such that said exogenous signal is transmitted from a source which is positioned proximate to at least one ear of the patient.

20. A method according to claim 1, wherein said delivering step is carried out such that said exogenous speech signal is transmitted from a location which is remote from the ear of the patient and travels through the air and into the ear of the patient while the patient is speaking, wherein the exogenous speech signal is generated by a portable compact and/or wearable device with an integral speaker.

21. A method according to claim 18, wherein said exogenous speech signal is adjustable by the patient so that the patient can select a desired signal duration, a desired prolonged voice gesture sound, and volume to be provided during said delivering step.

22. A method according to claim 15, wherein said delivering step includes the step of transmitting the exogenously generated speech signal from a communication device at a location that is remote from an ear receptacle thereof.

23. A method according to claim 1, wherein said exogenously generated speech signal comprises a plurality of electronically recorded predetermined spoken prolonged voice gesture speech signals, and wherein said delivering step comprises varying which of the prolonged voice gesture speech signals is delivered to the patient over time.

24. A method according to claim 1, wherein said exogenously generated speech signal comprises a stuttered spoken speech signal which is incongruous with the content of the speech provided by the patient during said producing step.

25. A method according to claim 1, wherein said exogenously generated speech signal comprises a prolonged vowel sound having a duration of at least about 2 seconds.

26. A method according to claim 15, wherein said delivering step is carried out by one of an over-the-ear, behind-the-ear and in-the-ear device.

27. A method according to claim 15, wherein said recording step is performed by recording said exogenously generated speech signal onto a compact disk.

28. A method according to claim 1, wherein said delivering step generates the prolonged voice gesture so that the speech signal has a duration that is less than 2 minutes and is intermittently repeated during said producing step with between about 10 seconds to about 2 minutes between successive delivering steps.

29. A method according to claim 15, wherein said delivering step is carried out by one of a portable hand held device or, a wireless communication device or telephone at a location that is remote from an ear receptacle thereof.

30. A method according to claim 15, wherein said delivering step is carried out by a device configured to be worn as one of a belt clip, watch, hat, lapel, jacket, and pin, which is adapted to be positioned, in operation, such that it is in audible communication with the patient and devoid of head or ear sets so as to directly transmit the signal from the device through the air and into the ear canal of the user.

31. A device to enhance the fluency of persons who stutter, comprising:

an audio storage medium comprising at least one predetermined exogenously generated auditory stimulus speech signal thereon, wherein the at least one predetermined auditory stimulus signal comprises at least one prolonged voice gesture;

a speaker operably associated with said audio storage medium;

a power source in communication with said audio storage medium and said speaker; and an activation switch operably associated with said power source;

wherein said auditory stimulus speech signal is configured to be repeatedly output to a user at desired times corresponding to at least one of during an episodic stuttering event on the part of the user, in advance of the production of speech by the user, and intermittently during the production of speech of the user to thereby provide an auditory stimulus to the user who stutters to enhance the fluency of speech thereof.

32. A device according to claim 31, wherein said auditory stimulus speech signal is configured to generate a prolonged voice gesture having a prolonged vowel sound with a duration of at least about 2 seconds, wherein said device further comprises a user input trigger switch operably associated with said speaker, and wherein said user input trigger switch is configured to accept user input to initiate a substantially immediate delivery of said auditory stimulus speech signal such that it is audible to the user.

33. A device according to claim 31, wherein said device further comprises a microphone and a signal processor configured to receive and analyze a speech signal generated by the user's speech.

34. A device according to claim 33, wherein said device is configured to automatically output said auditory stimulus speech signal to the user from said speaker based on an analysis of the user's speech, such that said auditory stimulus speech signal is provided with the user's speech for a duration of between about 2 seconds to 2 minutes, and is incongruous with the content of the user's speech, and wherein said auditory stimulus speech signal is delivered in a manner which allows the user to speak at a substantially normal speech pace.

35. A device according to claim 34, wherein, in operation, said device is configured to identify the initiation and termination of speech production by the user by monitoring the signal received by said microphone and said signal processor, and wherein said device is configured to intermittently output said auditory stimulus speech signal while the user is speaking so that the auditory stimulus signal has a duration that is less than about 2 minutes and so that successive auditory stimulus signals are output to the user temporally spaced apart with at least about 10 seconds between successive auditory signals.

36. A device according to claim 31, wherein said device is configured to provide said auditory stimulus speech signal intermittently during the user's speech, with the auditory stimulus speech signal providing at least one prolonged vowel sound having a duration of between about 2 seconds to about 2 minutes and in a manner which allows the user to speak at a substantially normal speech pace.

37. A device according to claim 36, wherein said auditory stimulus speech signal has a prolonged single syllabic vowel sound with a duration of at least about 5 seconds which is configured to be provided in advance of when the user speaks and/or intermittently while the user speaks.

38. A device according to claim 33, wherein said device further comprises a detector operably associated with said processor and said microphone, said detector configured to detect the onset of or an actual stuttering event, and wherein, in operation, upon recognition of the initiation of an impending or actual stuttering event on the part of the user, said device intermittently provides said auditory stimulus speech signal for a duration of between about 2 seconds to 2 minutes.

39. A device according to claim 31, wherein said auditory stimulus speech signal comprises a plurality of predetermined different exogenously generated auditory stimulus spoken speech signals, each having different prolonged voice gesture sounds, and wherein said plurality of different signals are configured to be serially output to the user at desired temporally spaced apart times with a plurality of prolonged voice gesture sounds in the different auditory stimulus signals having a duration of between about 2 seconds to 2 minutes.

40. A device according to claim 31, wherein said at least one auditory stimulus speech signal is a plurality of different exogenously generated auditory stimulus signals, each sound comprising at least one prolonged vowel sound having a duration of between about 2 seconds to about 2 minutes, the different auditory signals are configured to be are output to the user such that they are temporally separated in time.

41. A device according to claim 31, wherein said device is configured with a user activation switch which allows the device to provide said auditory stimulus speech signal in advance of and temporally proximate to the user speaking.

42. A device according to claim 31, wherein said auditory stimulus speech signal comprises at least one spoken prolonged single syllabic voice gesture sound.

43. A device according to claim 42, wherein each of said at least one prolonged voice gesture sounds is sustained in a substantially steady state audible range for at least about 5 seconds.

44. A device according to claim 31 wherein said auditory stimulus speech signal comprises a steady state /a/ vowel sound sustained in a substantially steady state audible range for at least about 5 seconds.

45. A device according to claim 31, wherein said auditory stimulus speech signal comprises a steady state consonant sound sustained in a substantially steady state audible range for at least about 5 seconds.

46. A device according to claim 31, wherein said exogenously generated auditory stimulus speech signal comprises a plurality of prolonged spoken voice gesture sounds including at least one of (a) a sustained vowel train sound lasting between about 2 seconds to 2 minutes, and (b) a sustained single vowel sound lasting between about 2 seconds to 2 minutes.

47. A device according to claim 31, wherein said exogenously generated auditory stimulus speech signal comprises a plurality of different prolonged vowel voice gesture sounds, each having a sustained audible duration which is at least about 10 seconds long.

48. A device according to claim 31, wherein said device is configured such that it is portable, and wherein, in use, said speaker is sized and configured to reside proximate the ear of the user such that said exogenously generated auditory stimulus speech signal is input into at least one ear of the user.

49. A device according to claim 31, wherein, during operation, said speaker is in audible communication with the user but is remotely located from the user such that said speech signal is output from said speaker in said device from a location away from the patient and then travels greater than about 3 inches through the air before entering into the ear of the patient while the patient is speaking, and wherein the device is a compact portable and/or wearable device with an integral speaker.

50. A device according to claim 31, wherein said device is incorporated into the body of a telephone away from an ear receptacle thereof.

51. A device according to claim 31, wherein said auditory stimulus speech signal is a recorded stuttered speech signal.

52. A device according to claim 31, wherein said auditory stimulus speech signal comprises a prolonged vowel sound recording provided by a person having normal fluency.

53. A device according to claim 31, wherein said device is configured as one of an over-the-ear, behind-the-ear, and in-the-ear device.

54. A device according to claim 31, wherein said audio storage medium is a compact disk.

55. A device according to claim 31, wherein said audio storage medium comprises a DSP.

56. A device according to claim 31, wherein said device is incorporated into one of a portable hand held device, a writing implement, and a wireless communication device or telephone at a location that is remote from an ear receptacle thereof.

57. A device according to claim 31, wherein said device is configured to be worn as one of a belt clip, watch, hat, lapel, jacket, eyeglass frame, and pin and so that the device is devoid of head or ear sets so as to directly transmit the signal from the device through the air and into the ear canal of the user.

58. A device according to claim 31, further comprising a remote control unit configured to activate the output of said auditory speech signal.

59. A product for enhancing the fluency of a person who stutters, comprising an audio storage medium comprising an exogenously generated speech signal including at least one prolonged voice gesture sound having a duration of between about 2 seconds to 2 minutes and generated by a person other than the person using the product to enhance their speaking fluency, wherein in operation, said exogenous speech signal is adapted to be relayed to a user as an auditory stimulus that is output intermittently to the user to enhance the fluency of the user who stutters.

60. A product according to claim 59, wherein the at least one prolonged voice gesture includes a predetermined prolonged vowel sound.

61. A product according to claim 60, wherein the prolonged vowel sound comprises a prolonged /a/ sound that has a duration of greater than 2 seconds.

62. A product according to claim 61, wherein the prolonged /a/ sound has a duration of at least about 5 seconds.

63. A product according to claim 59, wherein the at least one prolonged voice gesture comprises a prolonged sonorant sound.

64. A product according to claim 59, wherein the exogenous speech signal in the audio storage medium primarily comprises prolonged vowel and/or consonant sounds.

65. A product according to claim 59, wherein the exogenous speech signal in the audio storage medium consists essentially of prolonged voice gestures.

* * * * *